United States Patent [19]

Horrom et al.

[11] 4,375,478
[45] Mar. 1, 1983

[54] AMINOBENZOIC ACID DERIVATIVES

[75] Inventors: Bruce W. Horrom, Waukegan; Herman H. Stein, Skokie, both of Ill.

[73] Assignee: Abbott Laboratories, North Chicago, Ill.

[21] Appl. No.: 354,117

[22] Filed: Mar. 2, 1982

[51] Int. Cl.³ ............... A61K 31/195; C07C 101/60
[52] U.S. Cl. ............................ 424/319; 424/309; 560/47; 562/456
[58] Field of Search .......... 562/456, 458; 560/47; 424/309, 319

[56] References Cited

U.S. PATENT DOCUMENTS

| | | | |
|---|---|---|---|
| 3,787,478 | 1/1974 | Dolejs et al. | 562/456 |
| 3,868,416 | 2/1975 | Albright et al. | 562/456 |
| 4,185,115 | 1/1980 | Albright | 562/456 |
| 4,271,188 | 6/1981 | Hindley | 560/47 |
| 4,272,546 | 6/1981 | Shepherd | 560/47 |
| 4,310,545 | 1/1982 | Shepherd | 562/456 |

OTHER PUBLICATIONS

Albright et al., J. Pharm. Sci., vol. 68, #7, pp. 936-937, (1979).

*Primary Examiner*—James H. Reamer
*Attorney, Agent, or Firm*—Gildo E. Fato; Robert L. Niblack

[57] ABSTRACT

Described are compounds of the formula

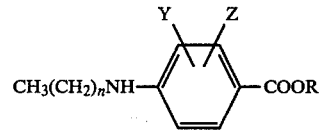

wherein Y and Z independently of one another denote hydrogen, halo or trihalomethyl, with the proviso that Y and Z cannot both be hydrogen, R is hydrogen or loweralkyl, n is 5 to 19, and pharmaceutically acceptable salts thereof.

The compounds are active hypocholesterolemic agents.

12 Claims, No Drawings

AMINOBENZOIC ACID DERIVATIVES

BACKGROUND OF THE INVENTION

Atherosclerotic plaque contains a high degree of cholesterol esters. It has been demonstrated in tissue culture studies that there is a close assocation between serum and cellular lipids in both human and calf endothelial cells (Ann. N.Y. Acad. Sci. 275:104, 1976). As a consequence, determinations of both cholesterol and triglycerides are recommended as part of every general medical examination. Lipid determinations are useful in confirming a diagnosis of primary hyperlipemia, in selecting the appropriate therapy and in assessing the efficacy of the selected treatment. It is apparent that control of serum lipid levels is desirable.

In addition to diet and weight reduction as a means of lowering serum lipid levels, it is known that some chemical compounds exhibit hypolipidemic activity. An example is sodium 4-(hexadecylamino)benzoate described in U.S. Pat. No. 3,868,416 issued Feb. 25, 1975. It is believed that the mechanism of action involves at least in part the inhibition of the enzyme acyl-coenzyme A:cholesterol acyl transferase (ACAT). This enzyme activity is responsible for the intracellular esterification of cholesterol, and it may play an important role in the pathogeneiss of atherosclerotic lesions. Inhibition of ACAT could result in an increased rate of removal of cholesterol from peripheral tissues by high density lipoproteins (HDL), and in this way an antiatherosclerotic effect would be achieved.

SUMMARY OF THE INVENTION

The present invention is directed to compounds of the formula

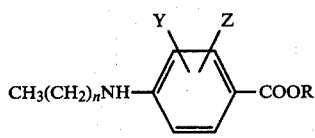

wherein Y and Z independently of one another denote hydrogen, halo or trifluoromethyl, with the proviso that Y and Z cannot both be hydrogen, R is hydrogen or loweralkyl, n is 5 to 19, and pharmaceutically acceptable salts thereof.

The compounds are active hypocholesterolemic agents.

The term "loweralkyl", as used herein, refers to straight or branched chain alkyl radicals containing from 1 to 6 carbon atoms, including, but not limited to methyl, ethyl, n-propyl, iso-propyl, n-butyl, sec-butyl, 2-methylbutyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg/kg per day per patient are useful, with the total dose of up to 0.5 to 5.0 gm per day being a suitable range for large animals, including humans.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

General methods for preparation of compounds of the type described herein are disclosed in U.S. Pat. No. 3,801,636 issued Apr. 2, 1974 and in particular in Example III thereof.

The following reaction scheme illustrates the preparation of a compound of the invention. While illustrating the preparation of a specific compound, other compounds of the invention can be made in the same manner.

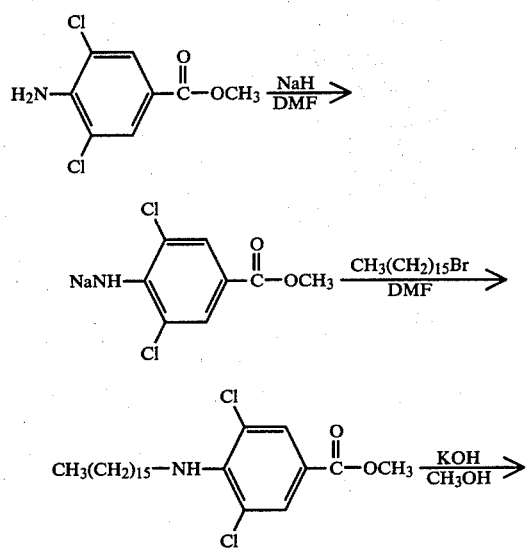

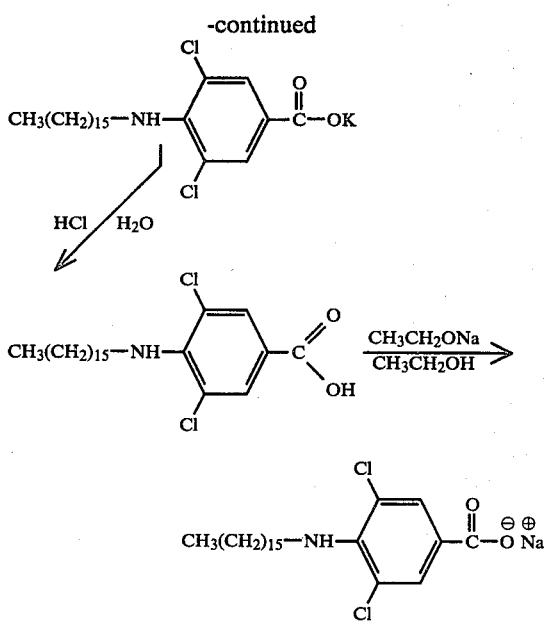

EXAMPLE 1

3,5-Dichloro-4-hexadecylamino benzoic acid 44 g (0.2 mole) of methyl-3,5-dichloro-4-amino benzoate in 50 ml of dimethylformamide was added dropwise, while stirring over a 15 minute period, to 5.20 g (0.21 mole) of sodium hydride in 100 ml of dimethylformamide while heating on a steam bath. After addition was complete the reaction mixture was heated 15 minutes longer. The bath was removed and while the reaction was still hot 64 g (0.21 mole) of n-hexadecyl bromide was added over a 15 minute period. After addition of the bromide was complete, the reaction mixture was heated for 1 hour on the steam bath and allowed to stand for 4 hours. Thereafter, the mixture was heated for an additional hour. The reaction mixture was then concentrated under vacuum and benzene was added along with water. The benzene solution was then washed 3 times with water (severe emulsions formed). The dark red benzene solution was dried over sodium sulfate and filtered through a hyflosupercell mat and concentrated. The crude methyl-(3,5-dichloro-4-hexadecylamino)benzoate weighed 82 grams. The dark brown oil had $n^{25}$ 1.5136 and the material was obtained in a 91.5% yield.

A small amount of the above crude ester was distilled b.p. 220° @ 0.1 mm, $n^{25}$ 1.5114; melting point 39°–41° C. Thin layer chromatography of the crude material and the distilled product both gave one spot material (hexane-19, EtoAC-1).

80 grams (0.18 mole) of the crude ester in 430 ml of methanol was hydrolyzed by the addition of 79 grams of potassium hydroxide in 85 ml of water. Most of the methanol was removed under vacuum and water was added to the potassium salt. This solution was filtered through a filtercell mat and the filtrate was acidified with 6 N HCl. The desired acid was obtained after filtering and drying, m.p. 92°–94°. This was recrystallized from methanol and water, m.p. 92°–94°.

Calculated for $C_{23}H_{37}Cl_2NO_2$ (percent). Theoretical: C, 64.17; H, 8.68; N, 3.25. Found (percent): C, 64.34; H, 9.03; N, 3.27.

EXAMPLE 2

Sodium (3,5-dichloro-4-hexadecylamino)benzoate

Sodium ethoxide was prepared from 2.1 g (0.09 mole) of sodium metal in 90 ml absolute ethanol. 16.5 g (0.038 mole) of 3,5-dichloro-4-hexadecylamino benzoic acid in 350 ml of absolute ethanol was added rapidly to the sodium ethoxide solution. The reaction mixture was then heated to reflux and filtered hot through a filtercell mat. The clear light yellow filtrate was then placed in the cold room for 48 hours. The resulting precipitate was filtered off. The solid was recrystallized from ethanol and water. On drying the product melted at 272°–274° C. as the hemihydrate.

Calcd. for $C_{23}H_{36}Cl_2NO_2Na.\frac{1}{2}H_2O$ (percent). Theoretical: C, 59.86; H, 8.08; N, 3.04. Found (percent): C, 59.70; H, 8.17; N, 2.97.

Acyl-coenzyme A: Cholesterl Acyl Transferase

Test Compound (final concentration = $1.0 \times 10^{-4}$ M) and 120 mcg of liver microsomal protein were preincubated for 5 minutes at 37° C. in 0.1 M phosphate buffer, pH 7.4, containing $6.0 \times 10^{-5}$ M bovine serum albumin and 0.002 M dithiothreitol (final volume = 0.189 ml). Oleoyl-1-$^{14}$C-coenzyme A, dissolved in buffer, was added in a volume of 0.011 ml so that the final concentration was $6.0 \times 10^{-5}$ M at a specific activity of 10.8 mCi/mmol (0.11 u Ci/tube). After incubation at 37° C. for 10 minutes, the reaction was stopped with the addition of 4.0 ml of chloroform:methanol at a ratio of 2:1 (C-M). The mixture was shaken after the addition of 0.84 ml of water, and the organic layer was evaporated to dryness. The aqueous phase was extracted again with 4.0 ml of C-M and the organic layer added to the dried residue of the first extractant. After evaporation, the residue was taken up in 0.040 ml of toluene:-chloroform (4:1) and 0.020 ml were spotted on a Silica Gel-G TLC plate, 250 u thickness.

The plate was developed in a hexane:diethyl ether:acetic acid solution (90:10:1) and the cholesterol oleate area was visualized with iodine vapor. The cholesterol oleate spot (Rf = 0.70) was scraped from the plate and counted in Packard Scinto Liquid. Samples were run in triplicate, and percent inhibition was calculated utilizing controls with sample solvent only. Compounds were dissolved in ethanol, and the final concentration in the incubation medium was 1.0% in the first experiment and 2.5% in the second.

Progesterone was utilized as a reference standard for ACAT inhibition (60% inhibition at $1.0 \times 10^{-4}$ M).

Plasma Lipoproteins Effects in Gerbils

Test compounds were suspended in 0.1% methylcellulose in isotonic saline at a concentration such that the desired dose was given in a volume of 4.0 ml/kg.

On the day before initiation of the experiment and on the day before the last dose, food was removed from the gerbils in the early evening, and at 9 a.m. the next day the animals were bled by heart puncture (0.5 ml) after light ether anesthesia; the animals were dosed approximately 2 hours after bleeding on Day 0 and 2 hours before bleeding on the last dosing day. The blood sample was mixed with a solution of EDTA, 50 mg/ml at pH 7.4, so that the final concentration was 1.5 mg/ml. After swirling, the contents were centrifuged at $1500 \times g$ for 10 minutes at 5° C. The plasma was removed from the packed cells and a portion was analyzed for cholesterol utilizing the ABA-100 and A-GENT cholesterol reagent. To 0.100 ml of another portion of plasma was added 0.010 ml of $Mg^{+2}$-phosphotungstate reagent (prepared daily by adding one part of $MgCl_2$, 1.5 M, and 4 parts of sodium phosphotungstate, 4%, adjusted to pH 7.4 with 1.0 N NaOH. The mixture was vortexed and allowed to remain at room temperature for 5 minutes. The sample was centrifuged at 100,000×g for 5 minutes and an aliquot of supernatant analyzed for HDL cholesterol (HDL-C). The difference between total plasma cholesterol and HDL-C (after correction for dilution) was utilized as an estimate of low density plus very low density lipoprotein cholesterol (LDL-C plus VLDL-C). Animals were treated for 5 days in the first experiment and for 4 days in the second.

Controls and test compounds were evaluated in groups of 12 gerbils. The significance of the changes in the plasma parameters was evaluated by a paired t-test; tests of hypothesis were performed at the 0.05 significance level.

Test Compounds

A: Progesterone
B: Sodium (3,5-dichloro-4-hexadecyl amino)benzoate
C: Sodium 4-(hexadecylamino)benzoate ACAT Assay Results obtained in the in vitro assay are recorded in Table 1. Compound A was more potent than compound B at both alcohol concentrations (84% and 74% inhibition versus 26% and 45% inhibition). At 1% alcohol compound B was not completely soluble while at 2.5% it was; the increased solubility may account for the greater inhibitory effect at 2.5% ethanol. Compound A was also more potent than progesterone which inhibited 65–66% at both alcohol concentrations, in good agreement with the literature value of 60%.

TABLE 1

Acyl-Coenzyme A:Cholesterol Acyl Transferase (ACAT) In Vitro

| Addition | Cholesterol Oleate CPM + S.D.[a] | Inhibition Percent |
|---|---|---|
| Ethanol, 1% | 2578 ± 473 | — |
| Progesterone 1.0 × 10$^{-4}$ M, Ethanol, 1% | 891 ± 555 | 65 |
| Compound B 1.0 × 10$^{-4}$ M, Ethanol, 1% | 419 ± 158 | 84 |
| Compound C 1.0 × 10$^{-4}$ M Ethanol, 1% | 1917 ± 33 | 26 |
| Ethanol, 2.5% | 1338 ± 218 | — |
| Progesterone 1.0 × 10$^{-4}$ M, Ethanol, 2.5% | 453 ± 61 | 66 |
| Compound B 1.0 × 10$^{-4}$ M, Ethanol, 2.5% | 345 ± 45 | 74 |
| Compound C 1.0 × 10$^{-4}$ M, Ethanol, 2.5% | 735 ± 187 | 45 |

[a]Counts per minute ± standard deviation.

Plasma Lipoprotein Effects in Gerbils

The results obtained in 2 separate experiments are listed in Table 2A and 2B.

TABLE 2A

Effect on Plasma Lipoproteins in Gerbils
Compound B Administered for Five Days[a]

| Test Compound | Before Test | After Test | Percent Change |
|---|---|---|---|
| Vehicle Control (4.0 ml/kg) | | | |
| Total Cholesterol[b] | 89.3 ± 21.1 | 77.8 ± 15.5 | −13[c] |
| HDL-C[b] | 48.3 ± 14.8 | 40.4 ± 9.8 | −16[c] |
| LDL-C plus VLDL-C[b] | 41.0 ± 11.4 | 37.3 ± 8.1 | −9[c] |
| Compound B (100 mg/kg) | | | |
| Total Cholesterol | 96.6 ± 12.9 | 77.7 ± 12.3 | −20[d] |
| HDL-C | 51.7 ± 11.1 | 42.0 ± 7.0 | −19[d] |
| LDL-C plus VLDL-C | 44.8 ± 7.1 | 35.8 ± 6.0 | −20[d] |

[a]One animal died in each group and 11 data pairs were analyzed.
[b]mg/dl ± standard deviation.
[c]No significant difference, p 0.05.
[d]Significant difference, p 0.05.

TABLE 2B

Effects on Plasma Lipoproteins in Gerbils
Compound B and Compound C Administered for Four Days[e]

| Test Compound | Before Test | After Test | Percent Change |
|---|---|---|---|
| Vehicle Control (4.0 ml/kg) | | | |
| Total Cholesterol | 94.3 ± 17.9 | 86.2 ± 10.7 | −8[c] |
| HDL-C | 54.3 ± 12.9 | 49.3 ± 9.9 | −9[c] |
| LDL-C plus VLDL-C | 40.0 ± 10.8 | 36.9 ± 8.9 | −8[c] |
| Compound B (123 mg/kg[f]) | | | |
| Total Cholesterol | 96.6 ± 20.3 | 81.0 ± 10.2 | −10[d] |
| HDL-C | 53.7 ± 9.9 | 48.8 ± 9.7 | −9[d] |
| LDL-C plus VLDL-C | 42.9 ± 16.8 | 32.1 ± 8.8 | −25[d] |
| Compound C (100 mg/kg) | | | |
| Total Cholesterol | 93.0 ± 13.3 | 90.0 ± 11.7 | −3[c] |
| HDL-C | 47.1 ± 13.4 | 45.1 ± 3.8 | −4[c] |
| LDL-C plus VLDL-C | 45.9 ± 15.3 | 44.9 ± 10.6 | −2[c] |

[c]No significant difference, p 0.05.
[d]Significant difference, p 0.05.
[e]One animal died in the control and Compound B groups and 11 data pairs were analyzed; 12 data pairs in the Compound C group.
[f]Molar equivalent of 100 mg/kg Compound C

What is claimed is:

1. A compound of the formula

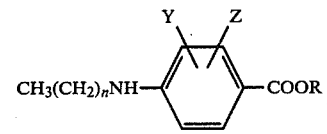

wherein Y and Z independently of one another denote hydrogen, halo or trihalomethyl, with the proviso that Y and Z cannot both be hydrogen, R is hydrogen or loweralkyl, n is 5 to 19, and pharmaceutically acceptable salts thereof.

2. A compound of claim 1 wherein Y and Z are trifluoromethyl.

3. A compound of claim 1 wherein Y and Z are each chloro, R is hydrogen and n is 15.

4. A compound of claim 1 wherein Y and Z are each chloro, R is sodium and n is 15.

5. A pharmaceutical composition having hypocholesterolemic properties comprising a hypocholesterolemically effective amount of a compound of the formula

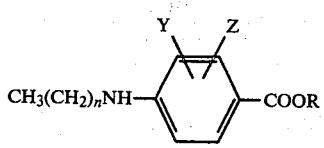

wherein Y and Z independently of one another denote hydrogen, halo or trihalomethyl, with the proviso that Y and Z cannot both be hydrogen, R is hydrogen or loweralkyl, n is 5 to 19, and pharmaceutically acceptable salts thereof and a pharmaceutically acceptable carrier.

6. A composition of claim 5 wherein Y and Z are trifluoromethyl.

7. A composition of claim 5 wherein Y and Z are each chloro, R is hydrogen and n is 15.

8. A composition of claim 5 wherein Y and Z are each chloro, R is sodium and n is 15.

9. A method of treating hypercholesteremia comprising administering to a patient in need of such treatment a therapeutically effective amount of an antihypercholesteremic agent of the formula

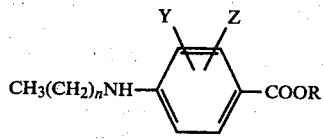

wherein Y and Z independently of one another denote hydrogen, halo or trihalomethyl, with the proviso that Y and Z cannot both be hydrogen, R is hydrogen or loweralkyl, n is 5 to 19, and pharmaceutically acceptable salts thereof.

10. The method of claim 9 wherein Y and Z are trifluoromethyl.

11. The method of claim 9 wherein Y and Z are each chloro, R is hydrogen and n is 15.

12. The method of claim 9 wherein Y and Z are each chloro, R is sodium and n is 15.

* * * * *